United States Patent [19]
Mascio

[11] Patent Number: 5,586,160
[45] Date of Patent: Dec. 17, 1996

[54] AUTOMATED ANALYSIS FOR MICROCALCIFICATIONS IN HIGH RESOLUTION DIGITAL MAMMOGRAMS

[75] Inventor: Laura N. Mascio, Dublin, Calif.

[73] Assignee: The Regents of the University of California, Oakland, Calif.

[21] Appl. No.: 407,557

[22] Filed: Mar. 20, 1995

[51] Int. Cl.⁶ ........................................................ A61B 6/00
[52] U.S. Cl. ............................................ 378/37; 364/413.13
[58] Field of Search .......................... 378/37; 364/413.13, 364/413.22

[56] References Cited

U.S. PATENT DOCUMENTS 5,365,429  11/1994  Carman ............................... 364/413.13
5,416,602   5/1995  Inga et al. ................................ 358/403

Primary Examiner—David P. Porta
Assistant Examiner—David Vernon Bruce
Attorney, Agent, or Firm—Henry P. Sartorio; John P. Wooldridge

[57] ABSTRACT

A method for automatically locating microcalcifications indicating breast cancer. The invention assists mammographers in finding very subtle microcalcifications and in recognizing the pattern formed by all the microcalcifications. It also draws attention to microcalcifications that might be overlooked because a more prominent feature draws attention away from an important object. A new filter has been designed to weed out false positives in one of the steps of the method. Previously, iterative selection threshold was used to separate microcalcifications from the spurious signals resulting from texture or other background. A Selective Erosion or Enhancement (SEE) Filter has been invented to improve this step. Since the algorithm detects areas containing potential calcifications on the mammogram, it can be used to determine which areas need be stored at the highest resolution available, while, in addition, the full mammogram can be reduced to an appropriate resolution for the remaining cancer signs.

18 Claims, 4 Drawing Sheets

AUTOMATED ANALYSIS FOR MICROCALCIFICATIONS IN HIGH RESOLUTION DIGITAL MAMMOGRAMS

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to the field of mammography, and more specifically, it relates to computerized analysis and compression of digital mammograms.

2. Description of Related Art

Detection and diagnosis of microcalcifications in mammograms is one of the most important and difficult tasks performed by radiologists. Early diagnosis and treatment of breast cancer, a leading cause of death in women, significantly improves the chances of survival. X-ray mammography is the only screening procedure with a proven capability for detecting early-stage, clinically occult breast cancers. Between 30% and 50% of breast carcinomas demonstrate microcalcifications on mammograms, and between 60% and 80% of breast carcinomas reveal microcalcifications upon microscopic examination. Therefore any increase in the detection of microcalcifications by screening mammography will lead to further improvements in its efficacy in the detection of early breast cancer in asymptomatic women. The American Cancer Society has recommended the use of mammography for screening of asymptomatic women over the age of 40 with annual examinations after age 50. For this reason, mammography may eventually constitute one of the highest volume X-ray procedures routinely interpreted by radiologists and with the highest volume of normals. Computer-aided detection and diagnosis may save the human radiologist time and tedium, especially on the "normal" images, so that more concentration can be dedicated to those cases that are clinically significant. The digital data will, however, require enormous amounts of storage space, and if full mammograms are stored at the highest possible resolution, less than 1% of the data will be clinically significant.

U.S. Pat. No. 4,907,156 describes a method and system for enhancement and detection of abnormal anatomic regions in a digital image. Classification schemes are used that are based on human-developed tests and thresholds which were designed to compromise on the number of true positives detected in order to minimize the number of false positive detections. The patent subtracts a signal-to-noise ratio (SNR)-suppressed image from a SNR-maximized image, but does not address the issue of compression at all. For signal extraction, the invention detects the boundary of the breast and performs a signal search only within the detected boundary. The classification scheme is based on pre-selected values determined from the clinical experience of radiologists and empirically by processing a number of test mammograms with known microcalcifications. As more digital radiographic imaging systems are developed, computer-aided searches become feasible. Successful detection schemes could eventually be hardware implemented for on-line screening of all mammograms prior to viewing by a physician.

Several investigators have attempted to classify and analyze detected mammographic abnormalities with digital computers. It is not clear whether these studies have achieved an accuracy acceptable for clinical practice, especially in the classification of microcalcifications. This failure can be attributed primarily to a large overlap in the features of benign and malignant lesions as they appear on mammograms.

The currently accepted standard of clinical care is such that biopsies are performed on 5 to 10 women for each cancer removed. Only with this high biopsy rate is there reasonable assurance that most mammographically detectable early carcinomas will be resected. Given the large amount of overlap between the characteristics of benign and malignant lesions on mammograms, computer-aided detection rather than characterization of abnormalities may eventually have greater impact in clinical care. Microcalcifications represent an ideal target for automated detection, because subtle microcalcifications are often the first and sometimes the only radiographic findings in early, curable, breast cancers, yet individual microcalcifications in a suspicious cluster (i.e., one requiring biopsy) have a fairly limited range of radiographic appearances.

The high spatial-frequency content and the small size of microcalcifications require that digital mammographic systems provide high spatial resolution and high contrast sensitivity. Digital mammographic systems that may satisfy these requirements are still under development. Digital radiographic systems with moderately high spatial resolution are made possible by fluorescent image plate/laser readout technology. Currently, digital mammograms with high resolution can be obtained by digitizing screen-film images with a drum scanner or other scanning system. The increasing practicability of digital mammography further underlines the potential ability of a computer-aided system for analysis of mammograms.

For electronically transmitting, storing and analyzing radiographs, mammograms remain the most challenging of all x-ray images because of the high resolution that is needed to accurately depict microcalcifications which are one of the three discrete abnormalities that indicates breast cancer. As a result, digitized mammograms can require about 50 megabytes of storage space per view, with 4 views per examination.

Data size reduction will be vital for the practical implementation of teleradiology systems (especially telemammography), since image size affects storage space, computer analysis time and transmittal times. Conventionally, there are lossless compression schemes which compress only at a ratio of 3:1, or there are lossy schemes which can compress to 30:1, but which must be tested exhaustively before they will be accepted in the medical community. Also, these schemes take time for compression as well as decompression. Image retrieval (even for viewing) is significantly slower if decompression must first take place.

A method of detecting microcalcifications indicating breast cancer is desirable. Such a method should include a reduction scheme which eliminates unnecessary information from the enormous amount of data in digital mammograms. It should achieve a reduction ratio of 10:1 to 30:1 without loss of appropriate resolution and with zero decompression time. It should use the context-based results of computer analysis to determine which areas of the mammogram must retain the highest resolution. All regions of the reduced mammogram should be capable of storage in a form that is ready-to-use and therefore does not impede retrieval times or viewing speeds. The present invention provides these advantages.

SUMMARY OF THE INVENTION

It is an object of the present invention to automatically detect, analyze and flag microcalcifications in digital mammograms.

It is another object of the invention to use knowledge from the automatic detection, analysis and flagging of microcalcifications in digital mammograms to reduce the size of the mammogram while retaining the appropriate information resolution required for accurate diagnosis in all areas of the mammogram.

Another object of the invention is to detect as many true positives as possible, even at the expense of false positive detections.

This invention provides computer-aided diagnosis capabilities enabled by the development of a computer algorithm using gray-scale morphology to automatically detect, analyze and flag microcalcifications in digital mammograms in hopes of reducing the current percentage of false-negative diagnoses, which is estimated at 20%. The mammograms used for developing this "mammographers assistant" are film mammograms that are digitized at either 70 μm or 35 μm per pixel resolution with 4096 (12 bits) of gray levels per pixel. For each potential microcalcification detected in these images, a number of features are computed in order to distinguish between the different kinds of objects detected.

A new filter has been designed to help weed out false alarms in one of the steps of the algorithm. Previously, an iterative selection threshold called the isodata threshold was used to separate microcalcifications from the spurious signals resulting from texture or other background. A Selective Erosion or Enhancement (SEE) Filter has been invented to improve this step.

Since the algorithm detects candidate microcalcifications in the mammogram, these local areas can be selectively stored at the highest resolution available, while the full mammogram is concurrently reduced and stored. In this way, the total size of the mammogram is reduced by a factor of 10 to 30, but all the abnormalities of clinical interest are appropriately depicted.

The foundation for this method is that the appropriate sampling rate for a mammogram varies throughout the image. For calcifications, it is generally accepted that a spatial resolution of 50 microns or better is required to retain fine shape parameters for computer analysis. For masses, spiculated lesions, and asymmetrical distortions, however, a spatial resolution of 200 microns or more has been effective for computer detection in clinical trials. For human observers inspecting film, there is evidence of similar trends since calcifications often warrant the use of a magnifying glass, but larger abnormalities are inspected without the magnifier and possibly even while standing back a distance from the mammogram.

The detection algorithm can be operated at a very high sensitivity level so as to detect and flag all possible areas of suspicion. The number of false alarms may be very high at this sensitivity, but that has little impact on the reduction technique. Storing even many extra areas at the full resolution will retain more information than is necessary and only mildly impact the amount of size-reduction achieved. The important thing is that no necessary information is lost. It is acceptable to store extra areas at the highest resolution, and that is emphasized in this scheme.

Once the mammogram has been reduced, it can be stored more cheaply, transmitted faster and analyzed faster by computer algorithms without time delays for decompression. Traditional compression algorithms take a full image, reduce it in size during storage, transmittal, etc., and then expand the image again, hopefully without loss of information. This method differs in that all areas of the mammogram are stored at the appropriate resolution and so need not be re-expanded for use.

Two high-frequency images are extracted from the original image and added together. By operating on the full area of the mammogram, the invention does not depend on the accuracy of those steps which limit the search range. A binary decision tree is used for classification. It is possible to simultaneously evaluate the usefulness of a number of features and the corresponding thresholds to retain all true positive detections. By employing the microcalcification detection results as part of a "dynamically lossless" or "selectively lossless" compression scheme, the size of the original mammogram is reduced, appropriate resolution for all regions in the mammogram are retained.

The compression scheme achieves ratios of 10:1 to 30:1 without loss of appropriate resolution and with zero decompression time. It uses the context-based results of computer analysis to determine which areas of the mammogram must retain the highest resolution. All regions of the reduced mammogram are stored in a form that is ready-to-use. Thus, retrieval times of viewing speeds are not impeded. Only those areas of the mammogram containing calcifications are stored at the highest resolution. The rest of the mammogram is stored in a reduced form. The reduced image can be used for detection of all abnormalities except calcifications. The high-resolution areas are the only areas that need be analyzed for calcifications.

DETAILED DESCRIPTION OF THE INVENTION

The microcalcification-detection algorithm of the present invention operates on digitized mammograms by combining morphological image processing with arithmetic processing to extract high frequency information. All kinds of microcalcifications are detectable with this method. It provides a sound platform for discriminating between suspicious and innocuous microcalcifications. The algorithm can analyze an entire mammogram in about 15 minutes, which includes running the algorithm with a Selective Enhancement or Erosion filter, and then implementing the results of the classification with a binary decision tree. The entire analysis is automated so there is no human interaction required for processing. The result is a normal mammogram with circled microcalcifications; interpretation and diagnosis is left for the mammographer.

The spatial resolution and dynamic range (gray-levels per pixel) required to adequately represent microcalcifications in a digitized film mammogram is an open question. Some loss of information for microcalcifications occurs at a sampling density of 100 µm, and it is generally accepted that at least 12 bits of detection resolution are also necessary to prevent loss of information. Yet, no published work is available on entire mammograms digitized at 100µm or smaller and with 12 bit detection resolution. Therefore, standard film/screen mammograms were digitized using an uncommon digitizer, described below, which can provide a spatial resolution as low as 35 µm per pixel and with 12 bits (4,096 gray levels) per pixel over an area the size of a full mammogram.

These sampling specifications increase computational and data management complexity, since a full mammogram can be as large as 50 MB at the highest resolution. Therefore, in order to demonstrate the computer-automated detection capabilities at these sampling specifications, computer capacity was increased as described below.

Conventional film mammograms were converted to digital format using a digitizer that was designed for precision industrial radiography by DuPont (Wilmington, Del.). It can be configured for a sampling density of 35 µm over a 7 inch by 17 inch area, or 75 µm over a 14 inch by 17 inch area. The detection resolution is 12 bits per pixel, or 4,096 gray levels. A full mammogram can be digitized and transferred to a workstation in about one minute.

Digitized images were analyzed on a DEC station 5000/200 (Digital Equipment Corporation, Maynard, Mass.) running the Ultrix operating system, version 4.2. The system was configured by maximizing the on-board random-access memory (RAM) to 192 MB and partitioning the hard drive with 396 MB of contiguous swap space. The software package used for analysis is SCIL-Image (Biological Detection Systems, Pittsburgh, Pa.). This package contains a C-interpreter built onto a comprehensive image processing library and uses the XWindow System for portability and remote analyses.

Figure 1:
FIG. 1 shows a portion of a digitized mammogram.

For a practical demonstration, only a small part of a full digitized mammogram will be used in the figures. FIG. 1 shows the small area of a digitized mammogram that will be used in the following discussion. According to a radiologist, this mammogram contains many benign microcalcifications and one cluster of three that should be monitored.

The microcalcification-detection algorithm begins by applying two high frequency analyses to an original digital image. It then combines the results so that high frequency information common to both analyses are enhanced and that which is common to only one method is de-emphasized. The two analyses are round high-emphasis and a mathematical morphology technique called texture gist analysis. Round high-emphasis and texture gist can be explained as follows.

Figure 2:
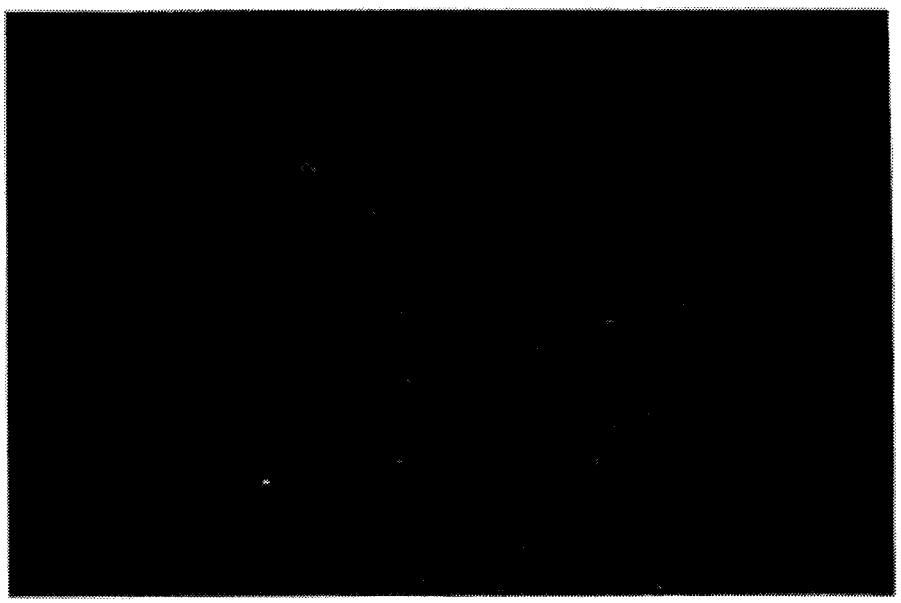
FIG. 2 is the image resulting from applying round-high emphasis to the original portion of the digitized mammogram shown in FIG. 1.

1. Round high-emphasis: This technique is a variation of the general method called unsharp masking. The theory for unsharp masking is that a low-pass filtered version of an image is subtracted from the image, leaving high frequency information. In the present case, the general theory is modified by using a round kernel with a diameter of 5 pixels to spatially average the original digitized image. The resulting image is then spatially averaged again with another round kernel of diameter 5 pixels. Recursively applying this operation with a small-diameter round kernel serves to thoroughly smooth the image while sufficiently maintaining the edges. The result is a low-pass-filtered version of the original image which preserves round edges. This low-frequency result is then subtracted from the original image leaving the high-frequency components of the image. FIG. 2 is the image resulting from applying round-high emphasis to the original portion of the digitized mammogram shown in FIG. 1.

Figure 3:
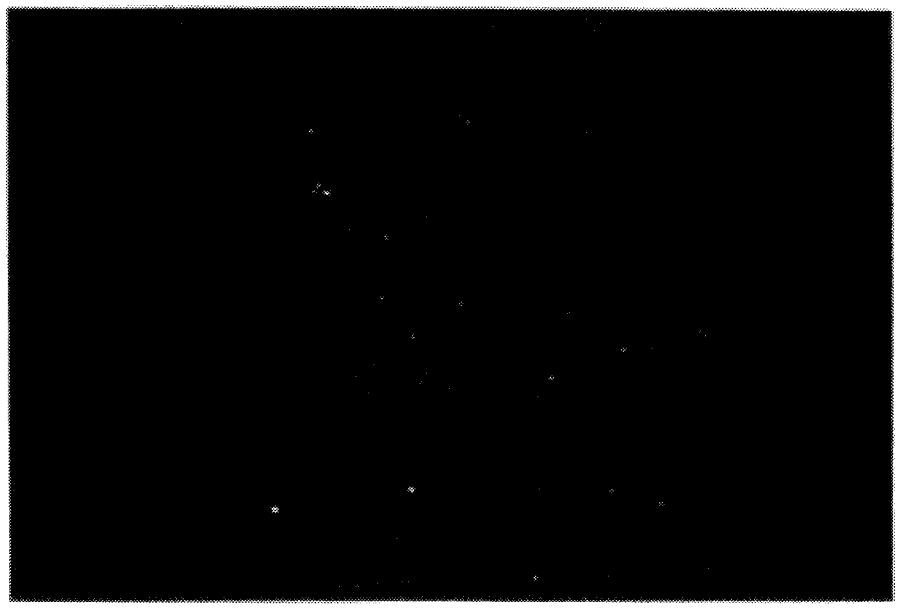
FIG. 3 is the image resulting from applying the texture gist algorithm to the original portion of the digitized mammogram shown in FIG. 1.

2. Texture gist: This method uses grayscale morphological operators to yield the upper and lower envelopes of an image. The operators are the minimum filter (MIN) which is a gray-level erosion, and the maximum filter (MAX) which is a gray-level dilation. The upper envelope is then MIN-(MAX) and the lower envelope is MAX(MIN). The two envelopes are averaged and the result is subtracted from the original image. FIG. 3 is the image resulting from applying the texture gist algorithm to the original portion of the digitized mammogram shown in FIG. 1.

Figure 4:
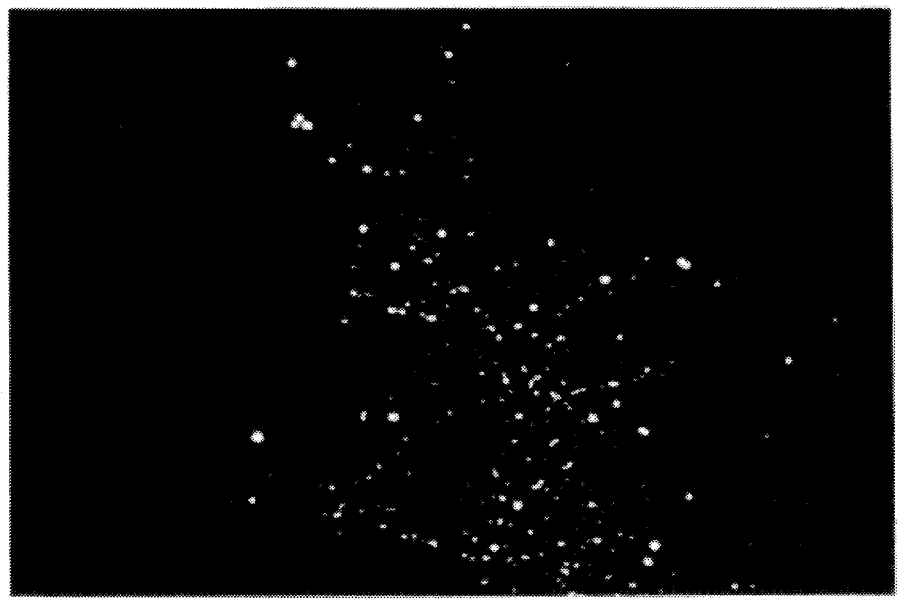
FIG. 4 is the resulting image from adding FIG. 2 and FIG. 3 and mapping the result back to 8 bits.

Both of these methods extract high frequency information from an image, but each emphasizes different aspects of frequency. The first emphasizes any detail in the image which changes sharply in intensity and is larger than several pixels in size. It will highlight streaks or thin lines in the image as well as bright spots. It will not emphasize very small, textured detail in the image which is not highly contrasting with the surroundings. The second method emphasizes detail in the image which is small and textured. Spatial frequency is the governing criterion for this technique. The texture gist will not emphasize lines or streaks, but it will highlight larger, brighter spots in addition to the flecks which make up the texture of tissue or other substances. Adding these images together yields an image which is brightest in locations containing detail common to both. FIG. 4 is the resulting image from adding FIG. 2 with FIG. 3, and mapping the result back to 8 bits.

The high frequency result is a gray-scale image, as was the original image, but now, the low-frequency detail is highly de-emphasized in the image. The next step is to segment the image so that all potential objects will be given an equal value and everything else is given a value of zero. A new filter has been designed to help weed out false alarms. This filtering step is used instead of the prior art thresholding step. The statistical threshold described above, attempted to separate true microcalcifications from the spurious signals resulting from texture or other background. Since then, a new Selective Erosion or Enhancement (SEE) Filter has been invented to improve this step. The SEE filter is more sophisticated than a single-value threshold because it adapts to different information from different parts of the image. Specifically, for every pixel in the image, the filter operation checks to see if the neighboring pixels are greater in value than the center pixel, or not. If a certain number (specified by a coefficient) of neighbors are greater in value than the center pixel, an average is taken of the pixels that are greater than the center pixel, and this average replaces the value of the center pixel. If there are not enough neighbors higher than the center pixel, then the center pixel is changed to a value of zero in the resulting image. In this way, pixels that are surrounding by strong pixels are reinforced. Pixels that are surrounded by weak pixels are removed. A description of the Selective Erosion or Enhancement Filter follows. Consider 9 points in an image arranged as follows:

| X | X | X |
|---|---|---|
| X | C | X |
| X | X | X |

Figure 5:
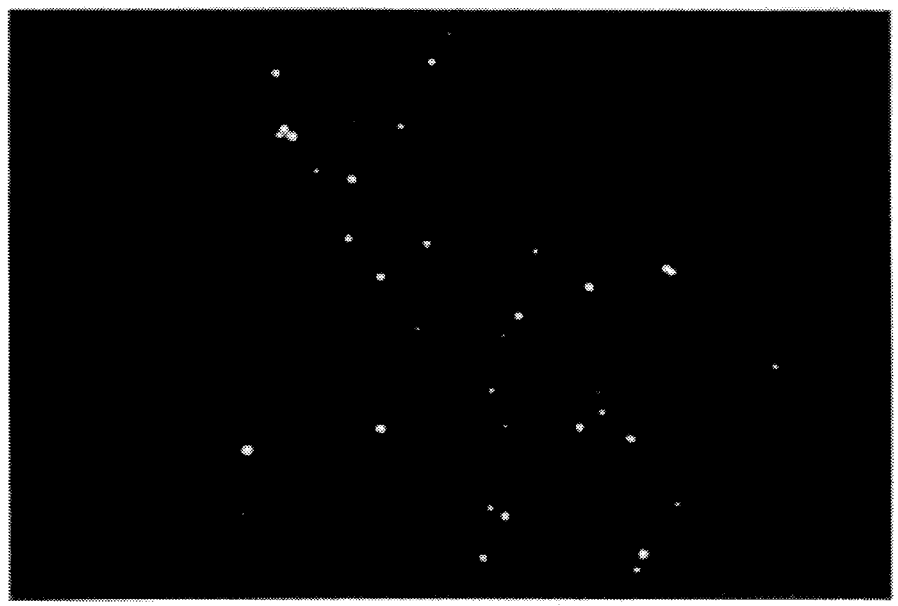
FIG. 5 is the image resulting from segmentation of the image of FIG. 4.

A coefficient K is chosen for a given application. The algorithm determines the number of Xs that are greater than or equal to C. If this number is greater than the coefficient K supplied, then C (in resulting image)=AVERAGE of ALL X>C. If this number is less than or equal to the coefficient supplied, then C (in resulting image)=0. In order to reduce the number of false positives, the segmentation masks (results from FIG. 5) are used to extract the potential microcalcifications from the original mammogram for feature extraction.

From the detected candidate objects, certain features are important in distinguishing between true microcalcifications and artifacts. The first steps of this algorithm served to detect likely microcalcifications and report their location. The method used for detection does not, however, segment, or define, the object shape exactly. Therefore, the next step is to return to each potential microcalcification and determine its extent more exactly. To do this consistently, each calcification was segmented in the following way: 1) The maximum intensity was detected in the candidate object; 2) the region immediately surrounding the object is thresholded at 80% of the maximum intensity value. In this way, all objects are defined so that their extent is defined consistently. A study was conducted which computed more than 60 measurements, or features, on detected and re-segmented microcalcifications and a binary decision tree was used to relate these measurements to a physician's diagnosis for thousands of microcalcifications. Due to the results of this study, each detected calcification is measured to make sure it is greater than 1 pixel in size and to make sure that it is not surrounded by more than 64 other detected objects. If these conditions are not met, the calcification is eliminated from the final group.

Figure 6:
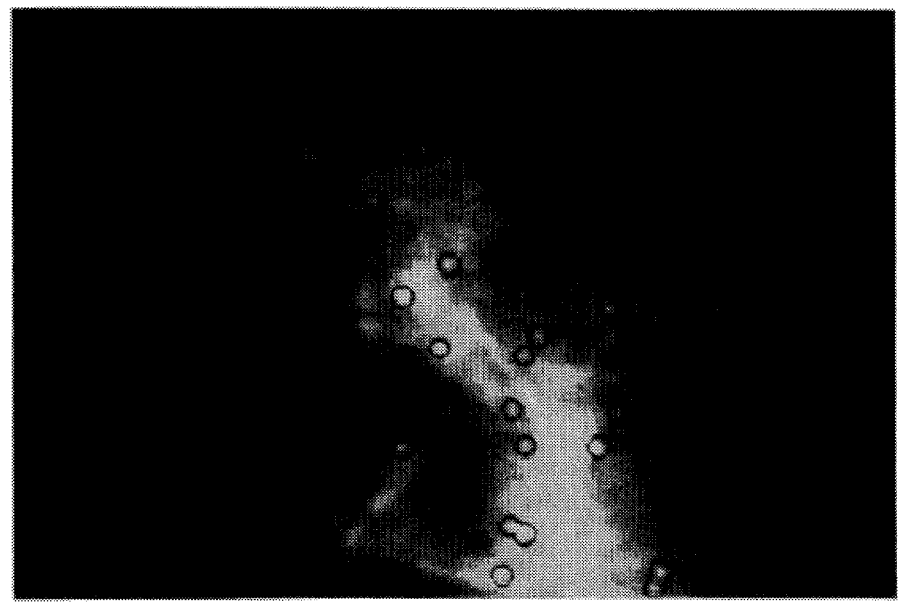
FIG. 6 is the final image with microcalcifications circled.

At this point, all potential microcalcifications are circled and presented to a mammographer for diagnosis, as shown in FIG. 6. The algorithm detected several microcalcifications which may have been missed by a radiologist. In addition, however, it found many false-positives in certain cases where tissue texture or film grain mimics the frequency information of microcalcifications. FIG. 6 is the resulting image with microcalcifications circled. All are almost certainly benign except possibly the cluster of three. The calcifications in the final group are highlighted and presented to a mammographer for subsequent diagnosis.

Since the algorithm detects microcalcifications (which are the smallest abnormality of all the early warning signs for breast cancer) and tends to err on the side of false positives, the algorithm can be applied to reduce the size of a mammogram by recognizing which areas need be stored at the highest resolution available, and which areas would be amenable to reduction.

For early detection of breast cancer, especially in younger women and women with "dense", glandular breasts, direct digital mammography and computer detection are emerging technologies. This inventions helps to fortify both technologies by developing a knowledge-based data compression scheme for mammograms. Reducing the data size of digital mammograms makes the clinical use of both digital mammography and computer detection efficient and practical. This compression technique includes an automated lossless scheme to reduce the data size of digital mammograms by a factor of 10 to 30. It retains all image detail by storing each region in a digital mammogram at its appropriate resolution. This approach has the advantage of zero decompression time for fast retrieval and display; optional output that is compatible with the DICOM standard; and much faster computer detection, especially for calcifications. Decreasing data size, without affecting diagnosis, ameliorates storage issues for all digital mammography screening units and makes computer-aided diagnosis palatable for commercial interests and clinical applications.

Compression algorithms are generally divided into two groups: lossless and lossy. Lossless schemes assure that the decompressed data values do not differ at all from the original, but the compression ratios achieved for mammograms are small (2:1 or 3:1 using lossless JPEG which is publicly available). Lossy schemes achieve much higher compression ratios (30:1), but do not result in exact restoration. Accordingly, they must be painstakingly proven before they will be accepted.

Further, traditional compression schemes require time for decompression when retrieving data for viewing or analysis. A commercially available wavelet-based compression scheme (Aware, Inc., Cambridge, Mass.) takes more than 30 seconds for decompression of one full mammogram, which affects retrieval and display speeds. Since current throughput for human inspection of mammograms is very rapid, such a retrieval delay is unacceptable in a clinical setting.

The automatic reduction scheme of the present invention uses mammogram-specific knowledge so that digital mammograms can be reduced in size by a factor of 10 to 30 with no loss of information and zero decompression time. The concept of "lossless" is extended to reflect the fact that the spatial resolution clinically required depends strongly on the type of abnormality to be detected. The appropriate sampling rate can vary throughout an image. For calcifications, it is generally accepted that a spatial resolution of 50 microns or better is required to retain fine shape parameters for computer analysis, and possibly even for computer detection. For masses, spiculated lesions, and asymmetrical distortions, however, a spatial resolution of 200 microns or more has been effective for computer detection in clinical trials. For human observers inspecting film, there is evidence of similar trends since calcifications often warrant the use of a magnifying glass, but larger abnormalities are inspected without the magnifier and possibly even while standing back a distance from the mammogram.

Therefore, "dynamically lossless compression" is defined to be a method that locally selects the spatial resolution necessary to adequately depict details needed for accurate detection. Storing detected calcifications at the highest resolution and other areas at their appropriate resolution achieves compression ratios of between 10:1 and 30:1. For all abnormalities, more resolution is retained here than is currently used by computer detection schemes described in the prior art. Because there is no decompression time necessary for this scheme and retrieval times are not impeded by decompression, the images are stored in a form ready-for-use. This will be of particular benefit for the first direct digital mammographic screening units, since one four-view case is on the order of 200 megabytes. For clinical use, there must be an efficient method for handling the huge amounts of data involved in mammogram screening.

This computer-detection scheme for calcifications can be operated at 100% sensitivity (for applications, such as the reduction scheme, where numerous false alarms are innocuous) and thus indicates all areas on a mammogram that contain calcifications. Using this knowledge of calcification location, the dynamically lossless compression algorithm retains appropriate resolution for all abnormalities while reducing data size by a factor of 10 to 30. The dynamically lossless compression algorithm is refined by determining the coarsest resolution that will adequately depict non-calcification features in order to yield the greatest size reduction.

Our data size reduction scheme uses the most sensitive setting for calcification detection. It converts one high resolution mammogram into one complete but coarser resolution mammogram and many high-resolution regions containing candidate calcifications. The scheme employs either a wavelet decomposition or resampling to downsize the original mammogram to one of coarser resolution. Initially, the coarseness of the resulting mammogram is varied between 110 and 280 microns to determine the coarsest adequate resolution for detecting non-calcification abnormalities. In all cases, regions containing calcifications are stored at the highest resolution available and the reduced mammogram will indicate these areas.

The computer detection of calcifications is much faster after reduction, since only those regions which contain possible calcifications need be inspected. Since calcifications are tiny in size compared to the size of the full mammogram, the candidate regions constitute a small fraction of the data size of the full mammogram. Computer detection of other abnormalities is much faster on the coarse image than on the fine one, but existing analysis programs are already utilizing images of the same size and resolution as the coarse image, so this reduction would have little effect on current analysis speeds for the larger warning signs.

In this invention, a whole mammogram is stored at 35 microns per pixel (50–60 Megabytes per file) because that is the resolution necessary to assure detection of the tiny microcalcifications. Once those areas containing calcifications are detected, the rest of the mammogram can be stored at 100–200 microns per pixel or more. This could reduce the storage requirements for a mammogram by a factor of 10 to 30. Of all the discrete signs of cancer, only microcalcifications require the highest resolution. Spiculated lesions, asymmetries and circumscribed masses are visible in images with much lower resolution.

Figure 7A:
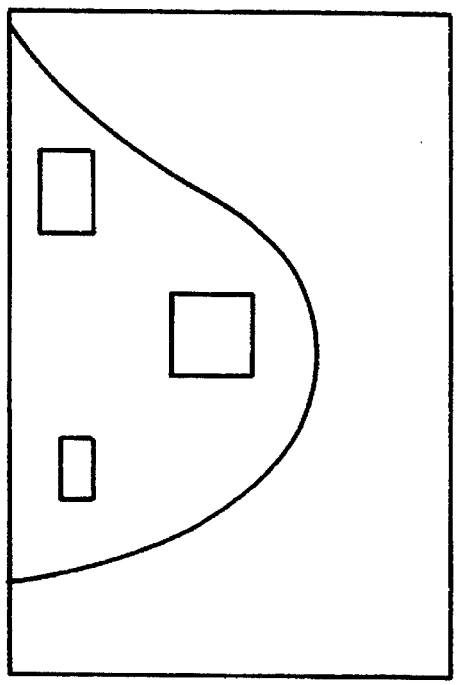
FIG. 7A depicts an original digital mammogram stored at 35 micron resolution.
Figure 7B:
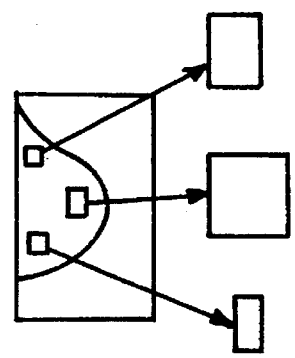
FIG. 7B depicts the mammogram of FIG. 7A after reduction to 100 micron resolution.

The locations indicated by the algorithm of this invention identifies those areas that need to be saved at high resolution. The rest of the image can be stored at much lower resolution. FIG. 7A depicts an original digital mammogram stored at 35 micron resolution (50 megabytes) with boxes 2, 4 and 6 around the results of the computer-aided detection of microcalcifications. FIG. 7B depicts the mammogram of FIG. 7A after reduction to 100 micron resolution (6 megabytes), which is sufficient for the other warning signs. In this figure, boxes 2, 4 and 6 are stored at the original 35 micron resolution necessary for detection of microcalcifications. The boxes stored at high resolution can be analyzed for microcalcifications by physicians or computers. When inspecting for other warning signs of cancer, the full mammogram stored at low resolution can be analyzed.

This technique will benefit archival systems in that it would save time and space in storage and retrieval. It would benefit transmittal systems in that the smaller image size would result in a faster transmission. And it would benefit computer-aided diagnosis systems for digital mammography in that it limits the image area to be analyzed for microcalcifications, thus improving analysis time. All of this would make digital mammography a closer and more practical reality for researchers and industrial partners.

Changes and modifications in the specifically described embodiments can be carried out without departing from the scope of the invention, which is intended to be limited by the scope of the appended claims.

I claim:

1. A method of detecting and highlighting microcalcifications in a digital mammogram, comprising:

applying round high-emphasis analysis to a digital mammogram to obtain a first image containing high-frequency information;

applying mathematical morphology to said digital mammogram to obtain a second image containing high-frequency information;

adding said first image and said second image and mapping the result to 8 bits to obtain a third image which is brightest in locations containing detail common to said first image and said second image;

applying a Selective Erosion or Enhancement Filter to reduce false positives indicated in said third image to produce a fourth image; and indicating the position of all potential microcalcifications on said fourth image to produce a final image.

2. The method of claim 1, wherein the step of applying round high-emphasis comprises:

spatially averaging said digital mammogram with a 5 pixel diameter round kernel to obtain a first spatially averaged image;

spatially averaging said first spatially averaged image with a 5 pixel diameter round kernel to obtain a second spatially averaged image; and subtracting said second spatially averaged image from said digital mammogram to obtain said first image containing high-frequency information.

3. The method of claim 2, further comprising recursively applying the step of spatially averaging said digital mammogram and the step of spatially averaging said first spatially averaged image to smooth said first image while maintaining edges of said first image.

4. The method of claim 1, wherein said mathematical morphology comprises a gray-scale morphology.

5. The method of claim 1, wherein said mathematical morphology comprises texture gist analysis.

6. The method of claim 5, wherein said texture gist analysis comprises:

averaging gray-level erosion with gray-level dilation to obtain a second averaged image; and subtracting said second averaged image from said digital mammogram to obtain said second image containing high-frequency information.

7. The method of claim 1, wherein the step of applying a Selective Erosion or Enhancement Filter comprises:

choosing a coefficient K;

determining, for every pixel in said third image, whether K neighboring pixels are greater in value than a center pixel;

replacing said center pixel with the average value of all neighboring pixels greater in value than said center pixel; and replacing said center pixel with a value of zero when the number of neighboring pixels around said center pixel is less than K.

8. The method of claim 1, wherein the step of applying a Selective Erosion or Enhancement Filter comprises:

removing pixels surrounded by weak pixels in said third image; and reinforcing pixels surrounded by strong pixels in said third image.

9. The method of claim 1, wherein the step of applying a Selective Erosion or Enhancement Filter comprises:

choosing a coefficient K, Wherein each pixel of said third image is a center pixel C, wherein pixels adjacent to C are X;

assigning a value to C that is equal to the average of all X when the number of X's that are greater than C is greater than K; and assign a value to C of zero when the number of X's that are greater than C is less than or equal to K.

10. The method of claim 1, further comprising:

storing all areas containing potential microcalcifications in said final image at the resolution of said digital mammogram to form a first stored image; and storing a reduced version of the entire final image to form a second stored image.

11. The method of claim 10, wherein said first stored image is stored at 35 microns, and wherein said second stored image is stored at a resolution within the range of 100 microns to 200 microns.

12. The method of claim 1, further comprising the step of reducing said final image, wherein the spatial resolution necessary to adequately depict details needed for accurate detection is locally selected.

13. The method of claim 1, further comprising the step of storing said potential microcalcifications indicated in said fourth image at the highest resolution, wherein the entire said final image is reduced to a resolution appropriate for non-calcification indications.

14. The method of claim 13, wherein said step for storing said potential microcalcifications indicated in said fourth image comprises an algorithm selected from a group consisting of a wavelet decomposition algorithm and a resampling algorithm.

15. The method of claim 1, further comprising the step of forming said digital mammogram at 70 micron per pixel resolution with 4096 gray levels per pixel.

16. The method of claim 1, further comprising the step of forming said digital mammogram at 35 micron per pixel resolution with 4096 gray levels per pixel.

17. The method of claim 1, further comprising the step of storing said potential microcalcifications indicated in said fourth image at a resolution of at least 50 microns, wherein the entire final image is reduced to a resolution of at least 200 microns for masses, spiculated lesions and asymmetrical distortions.

18. An apparatus for detecting and highlighting microcalcifications in a digital mammogram, comprising:

means for applying round high-emphasis analysis to said digital mammogram to obtain a first image containing high-frequency information;

means for applying mathematical morphology to said digital mammogram to obtain a second image containing high-frequency information;

means for adding said first image and said second image and mapping the result back to 8 bits to obtain a third image which is brightest in locations containing detail common to said first image and said second image;

means for applying a Selective Erosion or Enhancement Filter to reduce false positives indicated in said third image to produce a fourth image; and means for indicating the position of all potential microcalcifications on said fourth image to produce a final image.

* * * * *